US010436681B2

(12) United States Patent
Laugharn, Jr.

(10) Patent No.: US 10,436,681 B2
(45) Date of Patent: Oct. 8, 2019

(54) METHODS AND APPARATUS FOR TEMPERATURE CONTROL OF ACOUSTIC TREATMENT OF SAMPLES

(71) Applicant: Covaris, Inc., Woburn, MA (US)

(72) Inventor: James A. Laugharn, Jr., Boston, MA (US)

(73) Assignee: Covaris, Inc., Woburn, MA (US)

( * ) Notice: Subject to any disclaimer, the term of this patent is extended or adjusted under 35 U.S.C. 154(b) by 111 days.

(21) Appl. No.: 15/403,437

(22) Filed: Jan. 11, 2017

(65) Prior Publication Data

US 2017/0205319 A1    Jul. 20, 2017

Related U.S. Application Data

(60) Provisional application No. 62/279,130, filed on Jan. 15, 2016.

(51) Int. Cl.
*G01N 1/28* (2006.01)
*G01N 1/44* (2006.01)

(52) U.S. Cl.
CPC .............. *G01N 1/286* (2013.01); *G01N 1/44* (2013.01)

(58) Field of Classification Search
CPC ................................. G01N 1/286; G01N 1/44
USPC ............................................................ 436/177
See application file for complete search history.

(56) References Cited

U.S. PATENT DOCUMENTS 9,126,177 B2    9/2015  Laugharn, Jr. et al.
2012/0234625 A1*  9/2012  Laugharn, Jr. ......... G10K 11/28
                                                           181/140

* cited by examiner

*Primary Examiner* — Jill A Warden
*Assistant Examiner* — Jacqueline Brazin
(74) *Attorney, Agent, or Firm* — Wolf, Greenfield & Sacks, P.C.

(57) ABSTRACT

Methods and apparatus for transmitting acoustic energy to a liquid sample within a vessel are described. The acoustic energy may have a peak incident power to enhance cooling of the sample.

16 Claims, 2 Drawing Sheets

METHODS AND APPARATUS FOR TEMPERATURE CONTROL OF ACOUSTIC TREATMENT OF SAMPLES

CROSS REFERENCE TO RELATED APPLICATION

This application claims the benefit of U.S. Provisional Application No. 62/279,130, filed Jan. 15, 2016, which is hereby incorporated by reference in its entirety.

BACKGROUND

1. Field

Systems and methods for treating samples with acoustic energy are generally disclosed.

2. Related Art

Analytical techniques for biological and chemical samples often require an extreme physicochemical preparatory step to enable the desired analysis to be fully achieved. For example, extraction/digestion of herbicides and pesticides from plant tissue may require organic solvents (e.g., alcohols) and elevated temperatures (e.g., 50 degrees C.). This requirement to elevate the temperature of a sample to aid extraction of a desired component or constituent of a sample is a commonly used technique. For example, many environmental sample analysis techniques require thermal energy to aid extraction. Another area in which thermal energy is utilized to aid sample preparation is in microbial analysis; difficult cell wall disruption is aided by thermal energy.

Typically, transfer of thermal energy for such processes is achieved when heat is transferred from an area at higher temperature to a region of the sample at a lower temperature. For a biological or chemical sample contained in an isolated environment within a sample vessel, such heat transfer occurs by convection-based diffusion processes (Brownian motion and eddy diffusion) and advective fluid bulk transport (larger-scale current flow) processes which are inherently slow.

Acoustic energy-based sample processing devices, such as Adaptive Focused Acoustic apparatuses made by Covaris of Woburn, Mass., are effective for homogenization and disruption of biological tissues, cells and other sample material. With such devices, a controlled acoustic field enables repeatable processes to be developed which often result in higher recovery of target molecules. Such target molecules may be, for example, DNA, RNA, proteins, and the like. Target molecules or other materials may be contained as samples within a vessel.

SUMMARY

Aspects described herein relate to systems and methods for treating samples with focused acoustic energy. In particular, the focused acoustic energy may be applied to a sample in a manner that facilitates heat transfer between the sample and a wall of the vessel for cooling of the sample. For example, the inventor has surprising found that a sample may be more rapidly cooled by increasing a peak incident power (PIP) of acoustic energy applied to the sample. This result is unexpected because increasing the PIP of acoustic energy tends to cause more vigorous movement in the sample, thereby leading one to expect that the sample would heat due to increased friction. This, however, has not been found to be the case, such as where an increase in PIP by a factor of 10 was accompanied by more rapid cooling of a sample.

Enhanced cooling of a sample may be useful, for example, in processes that employ heating of a sample to enhance reaction rates, extracting compounds from a plant or animal tissue, disrupting cell walls, etc. That is, after a sample is exposed to elevated temperatures for a particular purpose, it may be useful to reduce the temperature of the sample, e.g., to stabilize the sample, render the sample safe for handling, etc. In some cases, the temperature of a sample may be elevated by application of acoustic energy, e.g., the acoustic energy may introduce friction in the sample and/or a vessel wall that holds the sample, thereby heating the sample. Thereafter, the temperature of the sample may be reduced, and may be mediated by acoustic energy. As noted above, increased PIP has surprisingly been found to enhance heat transfer from a sample.

In accordance with some aspects, a method for acoustic treatment of a sample contained in a vessel includes providing a vessel containing a liquid sample at a holder of an acoustic treatment apparatus. The vessel may have a wall in contact with a thermal transfer medium of the acoustic treatment apparatus, such as a liquid coupling medium, and the thermal transfer medium may have a thermal transfer medium temperature. The liquid sample may be exposed to a focused acoustic energy for a first period of time, with the focused acoustic energy being transmitted through the wall of the vessel to the liquid sample, and the focused acoustic energy having a peak incident power (PIP) and a duty cycle. The PIP of the focused acoustic energy may thereafter be increased during a second period of time to cool the liquid sample at a second rate that is faster than the first rate for the first period of time. The increased cooling rate may cause the temperature of the sample to be decreased, e.g., as heat is transferred from the sample to the thermal transfer medium.

In one embodiment, a method for acoustic treatment of a sample includes exposing a liquid sample to a first focused acoustic energy for a first period of time. The liquid sample may have a first temperature at an end of the first period of time, and the first temperature may be greater than the thermal transfer medium temperature. For example, in some embodiments, exposure of the sample to acoustic energy during the first period of time may cause the sample to be heated, e.g., to enhance certain reactions, inhibit operation of an enzyme or other reaction, etc. Thereafter, the liquid sample may be exposed to a second focused acoustic energy for a second period of time, and a second PIP of the acoustic energy during the second period of time may be being larger than a first PIP of the acoustic energy during the first period of time. In some embodiments, the liquid sample may have a second temperature at an end of the second period of time that is lower than the first temperature. That is, the sample may be cooled during the second period of time so that a temperature of the sample drops during the second period of time.

While heat may be transferred from the liquid sample to the thermal transfer medium during the first period of time at a first rate, heat may be transferred from the liquid sample to the thermal transfer medium during the second period of time at a second rate that is faster than the first rate. Thus, heat transfer from the sample need not be inhibited or prevented during the first period of time.

In some embodiments, a first total energy delivered to the liquid sample during the first period of time may be equal to or less than a second total energy delivered to the liquid sample during the second period of time. In addition, or alternately, a first average incident power for the first focused acoustic energy during the first period of time may be equal to or less than a second average incident power for the second focused acoustic energy during the second period of time. For example, the first average incident power for the first focused acoustic energy during the first period of time and the second average incident power for the second focused acoustic energy during the second period of time may both be less than 20 Watts. This can produce surprising results because although the total energy or average incident power may be the same or greater during the second period of time, the sample may be cooled at a higher rate than during the first period of time.

The thermal transfer medium temperature may be less than the second temperature, and/or the first temperature, e.g., so that heat may be transferred from the sample to the thermal transfer medium. In some embodiments, the thermal transfer medium may also function as a coupling medium to transfer acoustic energy from a source to the sample. For example, the thermal transfer medium may include liquid water in which a portion of the vessel is immersed. Also, the temperature of the thermal transfer medium may be adjusted or otherwise change, e.g., so as to be higher during the first period of time than the second period of time.

Features of the acoustic energy may vary for different embodiments, e.g., a volume of the liquid sample may be less than a volume of a focal zone of the first and second focused acoustic energies. Also, the first and second focused acoustic energies have a same, or different, cycles per burst, duty cycle or other characteristic.

As used herein, the total energy applied to a sample via acoustic energy is measured in Joules and given by the product of peak incident power (PIP in watts) by the duty cycle of the applied energy (DC in percentage terms) by the total processing time (T in seconds) or E=PIP*DC*T). Peak incident power (PIP) is the power emitted from an acoustic transducer or other source during the active period of one cycle. The peak incident power, in some cases, may control the amplitude of the acoustic oscillations. The acoustic transducer or other source may be operated at a suitable duty cycle (DC), in combination with other parameters, to generate focused acoustic energy that leads to preferred results. As described herein, the duty cycle is the percentage of time in a cycle in which the acoustic transducer or other source is actively emitting acoustic energy. For example, a duty cycle of 60% refers to the transducer being operated in an "on" state 60% of the time, and in an "off" state 40% of the time. The acoustic transducer or other source may also be operated according to a suitable cycles-per-burst (CPB) setting to achieve preferred results. As described herein, the cycles per burst (CPB) is the number of acoustic oscillations contained in the active period of one cycle. These parameters of PIP, DC and CPB may be varied in different acoustic treatment processes to achieve desired results.

Other advantages and novel features of the present disclosure will become apparent from the following detailed description of various non-limiting embodiments when considered in conjunction with the accompanying figures and claims.

BRIEF DESCRIPTION OF THE DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Figure 1:
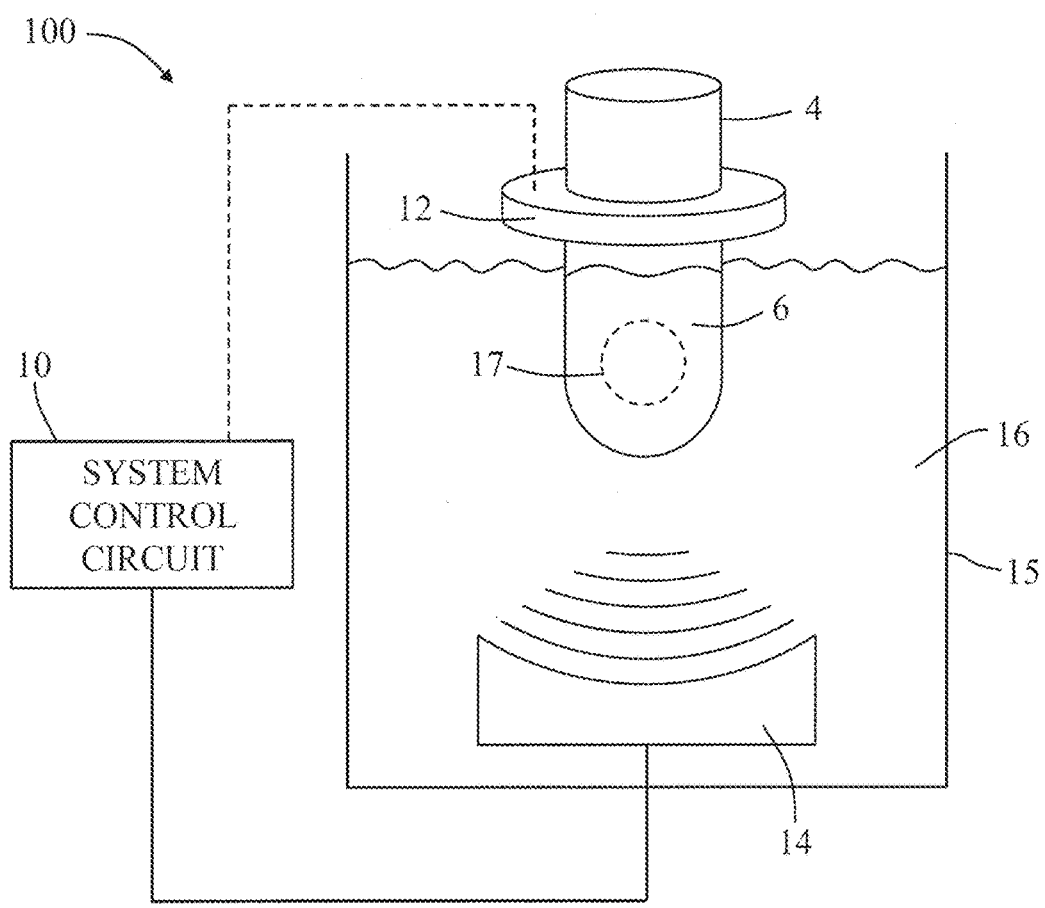
FIG. 1 shows a schematic block diagram of an acoustic treatment system that incorporates one or more aspects of the present disclosure.

Aspects of the present disclosure are not limited in application to the details of construction and the arrangement of components set forth in the following description or illustrated in the drawings. Other embodiments may be employed and aspects of the present disclosure may be practiced or be carried out in various ways. Also, the phraseology and terminology used herein is for the purpose of description and should not be regarded as limiting.

FIG. 1 shows a schematic block diagram of an acoustic treatment system 100 that incorporates one or more aspects of the present disclosure and/or can be employed with one or more aspects of the described herein. It should be understood that although embodiments described herein may include most or all aspects of the invention(s), aspects of the invention(s) may be used alone or in any suitable combination with other aspects of the invention(s).

In this illustrative embodiment, the acoustic treatment system 100 includes an acoustic energy source with an acoustic transducer 14 (e.g., including one or more piezoelectric elements) that is capable of generating an acoustic field (e.g., at a focal zone 17) suitable to cause mixing, e.g., caused by cavitation, and/or other effects on a liquid sample 6 contained in a vessel 4. As described in more detail below, the liquid sample 6 may include solid particles or other material dissolved, dispersed, or otherwise provided in a liquid material. Acoustic energy may be transmitted from the transducer 14 to the vessel 4 through a coupling medium 16, such as a liquid (e.g., water), a gel or other semi-solid, or a solid, such as silica, metal or other material, or combination of materials. Where the coupling medium 16 is a liquid, a coupling medium container 15 may be used to hold the coupling medium 16.

The vessel 4 may have any suitable size or other arrangement, e.g., may be a glass or metal tube, a plastic container, a well in a microtiter plate, a vial, or other, and may be supported at a location by a vessel holder 12. Although a vessel holder 12 is not necessarily required, the vessel holder 12 may interface with the control circuit 10 so that the vessel 4 and the sample in the vessel is positioned in a known location relative to an acoustic field, e.g., so that the focal zone 17 of the acoustic energy is located within the liquid sample 6. It should be understood that the vessel 4 may have any suitable shape, size, or other features, and may be made from any suitable materials. For example, the vessel 4 may be a cylindrical tube with a rounded bottom. The vessel 4 may be formed of glass, plastic, metal, composites, and/or any suitable combinations of materials, and formed by any suitable process, such as molding, machining, stamping, and/or a combination of processes. Also, the vessel holder 12 need not necessarily be capable of moving the vessel 4, and may be incorporated with the coupling medium 16. For example, the coupling medium 16 may include a solid material that has a pocket or other area defined to hold the vessel 4 in a particular position. It should also be noted that the coupling medium 16 may function as a waveguide or other functional part that focuses or otherwise has an effect on the acoustic energy emitted by the transducer 14.

The transducer 14 can be formed of a piezoelectric material, such as a piezoelectric ceramic. In some embodiments, the ceramic may be fabricated as a "dome," which tends to focus the energy. One application of such materials is in sound reproduction; however, as used herein, the frequency is generally much higher and the piezoelectric material would be typically overdriven, that is, driven by a voltage beyond the linear region of mechanical response to voltage change, to sharpen the pulses. Typically, these domes have a longer focal length than that found in lithotriptic systems, for example, about 20 cm versus about 10 cm focal length. Ceramic domes can be damped to prevent ringing or undamped to increase power output. The response may be linear if not overdriven. The high-energy focus zone of one of these domes may be cigar-shaped. At 1 MHz, the focal zone is about 6 cm long and about 2 cm wide for a 20 cm dome, or about 15 mm long and about 3 mm wide for a 10 cm dome. The peak positive pressure obtained from such systems is about 1 MPa (mega Pascal) to about 10 MPa pressure, or about 150 PSI (pounds per square inch) to about 1500 PSI, depending on the driving voltage. The focal zone, defined as an area or volume having an acoustic intensity within about 6 dB of the peak acoustic intensity, is formed around the geometric focal point. It is also possible to generate a line-shaped focal zone, e.g., that spans the width of a multi-well plate and enables the system 100 to treat multiple samples simultaneously. Other arrangements for producing focused acoustic energy are possible. For example, a flat transducer may be provided with a tapered waveguide (e.g., formed as part of the coupling medium 16) for focusing or otherwise channeling acoustic energy emitted from the transducer toward a relatively small space where the sample and vessel are located.

To control an acoustic transducer 14, the acoustic treatment system 100 may include a system control circuit 10 that controls various functions of the system 100 including operation of the acoustic transducer 14. For example, the system control circuit 10 may provide control signals to a load current control circuit, which controls a load current in a winding of a transformer. Based on the load current, the transformer may output a drive signal to a matching network, which is coupled to the acoustic transducer 14 and provides suitable signals for the transducer 14 to produce desired acoustic energy. Moreover, the system control circuit 10 may control various other acoustic treatment system 100 functions, such as positioning of the vessel 4 and/or acoustic transducer 14, receiving operator input (such as commands for system operation), outputting information (e.g., to a visible display screen, indicator lights, sample treatment status information in electronic data form, and so on), and others. Thus, the system control circuit 10 may include any suitable components to perform desired control, communication and/or other functions. For example, the system control circuit 10 may include one or more general purpose computers, a network of computers, one or more microprocessors, etc. for performing data processing functions, one or more memories for storing data and/or operating instructions (e.g., including volatile and/or non-volatile memories such as optical disks and disk drives, semiconductor memory, magnetic tape or disk memories, and so on), communication buses or other communication devices for wired or wireless communication (e.g., including various wires, switches, connectors, Ethernet communication devices, WLAN communication devices, and so on), software or other computer-executable instructions (e.g., including instructions for carrying out functions related to controlling the load current control circuit as described above and other components), a power supply or other power source (such as a plug for mating with an electrical outlet, batteries, transformers, etc.), relays and/or other switching devices, mechanical linkages, one or more sensors or data input devices (such as a sensor to detect a temperature and/or presence of the medium 16, a video camera or other imaging device to capture and analyze image information regarding the vessel 4 or other components, position sensors to indicate positions of the acoustic transducer 14 and/or the vessel 4, and so on), user data input devices (such as buttons, dials, knobs, a keyboard, a touch screen or other), information display devices (such as an LCD display, indicator lights, a printer, etc.), and/or other components for providing desired input/output and control functions.

Under the control of a control circuit 10, the acoustic transducer 14 may produce acoustic energy within a frequency range of between about 100 kilohertz and about 100 megahertz such that the focal zone 17 has a width of about 2 centimeters or less, though the focal zone 17 may be larger than 2 cm in other embodiments, as the current disclosure is not so limited. The focal zone 17 of the acoustic energy may be any suitable shape, such as spherical, ellipsoidal, rod-shaped, or column-shaped, for example, and be positioned within the liquid sample 6. The focal zone 17 may have a volume that is smaller than the volume of the liquid sample, and the focal zone may be entirely contained within the liquid sample 6 and spaced from the wall of the vessel 4, as shown in FIG. 1, or may be larger than the volume of the sample 6. U.S. Pat. Nos. 6,948,843 and 6,719,449 are incorporated by reference herein for details regarding the construction and operation of an acoustic transducer and its control.

Any suitable sample material can be included in a vessel, and the sample may include any suitable combination of a liquid (such as a solvent), a solid material (such as pieces of bone, tissue or plant materials), a dissolved material (such as a salt) and so on. Some example materials that may be included in a sample are DNA, RNA, nucleic acids, or other genetic material, antibodies, receptors and/or ligands associated with cellular functions, proteins, polymers, amino acid monomers, an amino acid chain, enzymes, nucleic acid monomers or chains, saccharides or polysaccharides, lipids, organic or inorganic molecules, vectors, plasmids, pharmaceutical agents, compositions suitable for crystal growth, prions, bacteria, and/or viruses. This is not intended to be an exhaustive list, but rather to provide a few examples of sample material that may be used with aspects of the present disclosure.

In accordance with an aspect of the present disclosure, the acoustic energy used to treat a sample in a vessel may be controlled so as to enhance heat transfer from the sample. For example, the sample may transfer heat to the vessel wall, and from the vessel wall to a thermal transfer medium (such as an acoustic coupling medium), and such heat transfer may be enhanced by increasing a peak incident power (PIP) of the acoustic energy used to treat the sample. This is a counterintuitive result because increasing a peak incident power is generally associated with increased heating of a sample resulting from the increased instantaneous energy introduced to the sample by the acoustic energy. However, the inventor has found that increasing the PIP can actually increase heat transfer from the sample. In some embodiments, an average incident power applied to the sample by the acoustic energy may remain the same or increase during a period that heat transfer from the sample is enhanced. For example, a sample may be treated with acoustic energy having a first average incident power during a first time period, and during this first time period a temperature of the sample may remain relatively constant or increase. Thereafter, the sample may be treated during a second time period with acoustic energy having a second average incident power that is the same as or greater than that of the first time period, and yet heat transfer from the sample may be enhanced such that a temperature of the sample is reduced. (The average incident power (AIP) is determined by multiplying the PIP by the duty cycle (DC), or AIP=PIP*DC.) Other conditions related to heat transfer, such as a temperature of a thermal transfer medium, may remain the same for both the first and second time periods. For example, the thermal transfer medium may have a constant temperature throughout the first and second time periods. Again, this is a surprising result because increased heat transfer would not be expected where an average incident power remains constant or is increased.

In some cases, a first total energy delivered to the liquid sample during a first time period of acoustic treatment may be equal to or less than a second total energy delivered to the liquid sample during a second time period of acoustic treatment. (The total energy delivered (TE) is determined by multiplying the PIP by the duty cycle (DC) and the time duration of the time period (T), or TE=PIP*DC*T.) Again, this is a counterintuitive result where a total energy delivered during the second time period in which a temperature of the sample is reduced, or decreases at a rate faster than during the first time period, is equal to or greater than that during the first time period.

In one illustrative embodiment, a method for acoustic treatment of a sample contained in a vessel includes providing a vessel containing a liquid sample and having a wall in contact with a thermal transfer medium. For example, the vessel 4 in FIG. 1 may be provided having a wall in contact with the coupling medium 16, which may function as a thermal transfer medium. The coupling medium 16 may have a coupling medium temperature that is below a temperature of the sample 6 in the vessel, at least before acoustic treatment begins or at some point during treatment. The liquid sample 6 may be exposed to a focused acoustic energy for a first period of time, and the focused acoustic energy may be transmitted through the coupling medium 16 and the wall of the vessel 4 to the liquid sample 6. The focused acoustic energy during the first time period may have a peak incident power (PIP) and a duty cycle, and may be employed for any suitable purpose, such as mixing the sample, homogenizing the sample, lysing cells, shearing DNA or other nucleic acid materials, heating the sample, etc. During the first time period, the temperature of the sample may remain relatively constant, or may increase. Where the temperature of the sample 6 is greater than the coupling medium 16 at some point during treatment, heat generated in the sample, such as by the acoustic energy, chemical reactions in the sample, etc., may be equal to or greater than a rate of heat loss to the coupling medium 16 so that the temperature of the sample 6 increases or remains constant.

During a second time period, the PIP of the focused acoustic energy may be increased relative to that of the first time period to cool the liquid sample and/or increase a rate of heat transfer from the sample. In some cases, the PIP may be increased by a factor of 2, 4, 10 or more. The duty cycle during the second time period may remain the same as during the first time period, or may be reduced, e.g., by a factor equal to the factor by which the PIP is increased. By employing a same factor to increase the PIP and decrease the duty cycle, a same average incident power may be applied to the sample during the first and second time periods. However, despite the increased PIP applied to the sample, a temperature of the sample may be decreased during the second time period. For example, a rate of heat transfer from the sample to the thermal transfer medium (in this case the coupling medium 16) may be greater than a rate of heat production in the sample (e.g., due to friction) so that the temperature of the sample is reduced. A ratio of the rate of heat transfer from the sample to the thermal transfer medium to the rate of heat production in the sample may be greater for the second time period than for the first time period, and these conditions may exist despite the fact that the PIP is increased and other factors related to thermal transfer remain the same, e.g., the thermal transfer medium temperature may remain constant. Also, the thermal transfer medium temperature may be less than the sample temperature during both the first and second time periods.

Figure 2:
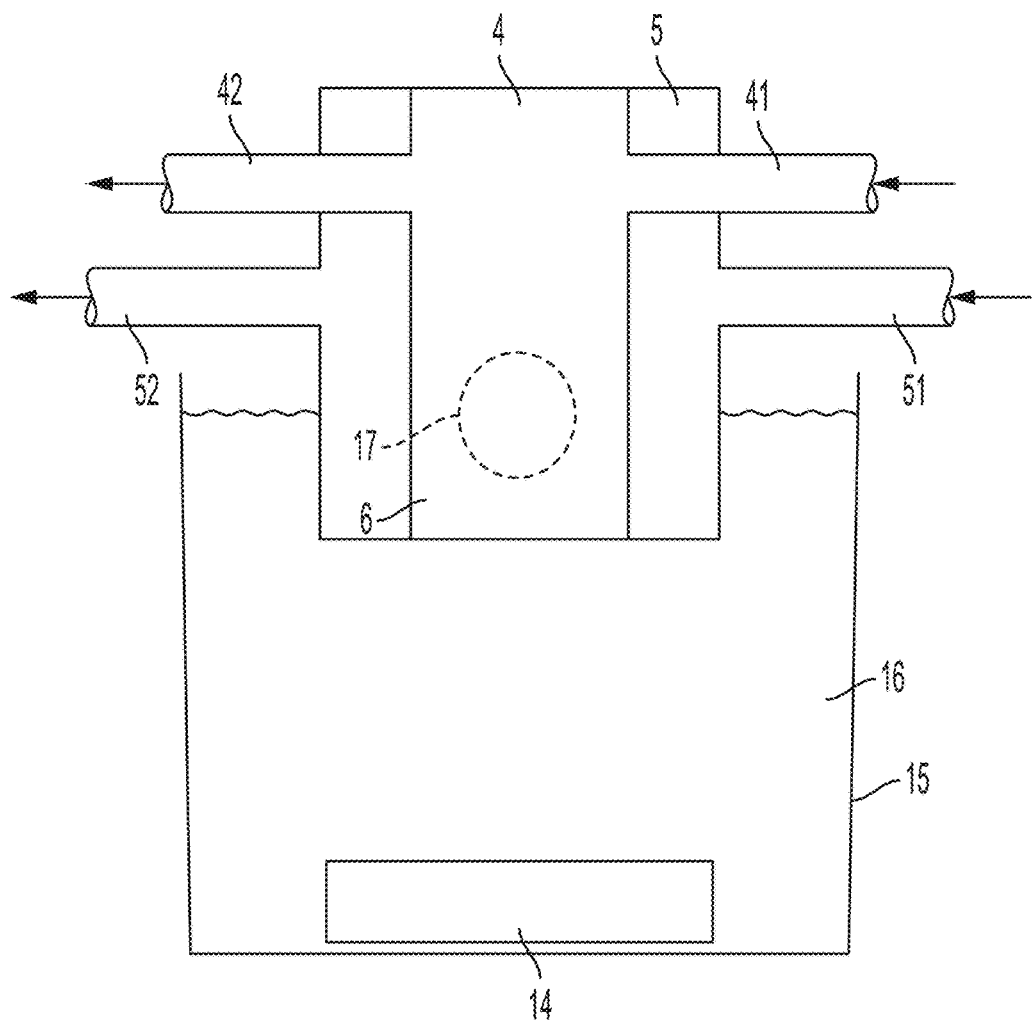
FIG. 2 depicts a schematic representation of an alternate acoustic treatment system according to some aspects of the present disclosure.

In another illustrative embodiment, a method for acoustic treatment of a sample contained in a vessel includes providing a vessel containing a liquid sample and having a wall in thermal contact with a thermal transfer medium of the acoustic treatment apparatus. As noted above, the thermal transfer medium may be a coupling medium that serves to transmit acoustic energy from an acoustic energy source to the vessel. In other embodiments, the thermal transfer medium need not transmit acoustic energy, but instead may function only to receive heat from the sample, e.g., by way of the vessel wall. For example, FIG. 2 shows an illustrative embodiment in which a vessel 4 containing a sample 6 is at least partially surrounded by a cooling jacket 5. (Portions of the FIG. 2 embodiment not discussed in detail herein may be arranged as discussed with respect to FIG. 1.) In this embodiment, the cooling jacket 5 includes a transfer medium inlet 51 and a transfer medium outlet 52 to allow a cooling fluid, such as water or a glycol solution, to be circulated through the cooling jacket 5. The cooling fluid may receive heat from the vessel wall to remove heat from the sample 6 and may have a relatively constant temperature and flow rate through the cooling jacket 5. Of course, the cooling fluid need not be circulated but may remain static in the cooling jacket 5. In addition, or alternately, a cooling fluid need not be used at all, and other arrangements for receiving heat, such as one or more heat sinks, heat pipes, thermoelectric devices, and/or other arrangements may be used to receive heat from the sample.

The liquid sample may be exposed to a first focused acoustic energy for a first period of time with the first focused acoustic energy being transmitted through the vessel to the liquid sample. Similar to that discussed above, the first focused acoustic energy may have a first peak incident power (PIP) and a first duty cycle, and the liquid sample may have a first temperature at an end of the first period of time. The first temperature may be greater than the temperature of the thermal transfer medium temperature, e.g., so that heat is transferred from the sample to the thermal transfer medium. However, in some cases, the rate of heat transfer may not be greater than a rate of heat production at the sample such that the temperature of the sample does not drop over the first period of time. For example, in some cases the sample may be heated to enhance a rate of one or more reactions in the vessel. That is, the acoustic energy may be used, at least in part, to heat the sample to activate or inactivate an enzyme-mediated reaction, to enhance thermally-mediated reactions or other processes, etc. Of course, the acoustic energy may be used for any suitable purpose, including mixing, homogenization, etc., and heating of the sample may by an undesirable byproduct.

To cool the sample, the liquid sample may be exposed to a second focused acoustic energy for a second period of time with the second focused acoustic energy being transmitted through the vessel to the liquid sample. The second focused acoustic energy may have a second peak incident power (PIP) and a second duty cycle with the second PIP being larger than the first PIP. In some cases, the second PIP may be 2, 4, 10 or more times greater than the first PIP. The liquid sample may have the first temperature at a start of the second period of time and a second temperature at an end of the second period of time that is lower than the first temperature. That is, the liquid sample may drop in temperature over the second time period during which acoustic energy having a greater PIP is employed.

It should be noted that during the first time period, heat may be transferred from the liquid sample to the thermal transfer medium, e.g., at a first rate, but this first rate may be low relative to a rate of heat generation at the sample such that the temperature of the sample remains constant or increases. However, during the second time period, heat may be transferred from the liquid sample to the thermal transfer medium at a second rate that is faster than the first rate. This increased heat transfer rate is believed to be due to the increased PIP employed in the second time period. The duty cycle of the acoustic energy during the first and second time periods may be the same or different, e.g., the first duty cycle may be greater than the second duty cycle. As discussed above, a first total energy delivered to the liquid sample during the first time period may be equal to or less than a second total energy delivered to the liquid sample during the second time period, and yet a heat transfer rate for the sample may be greater during the second time period. Similarly, a first average incident power for the first focused acoustic energy during the first time period may be equal to or less than a second average incident power for the second focused acoustic energy during the second time period. For example, the first average incident power and the second average incident power may both be less than 20 Watts, less than 50 Watts, or less than 100 Watts.

In some embodiments, the sample may be contained in a closed tube, like that shown in FIG. 1, and may have a relatively small volume, e.g., of 10 milliliters or less. In some cases, the volume of the liquid sample may be less than a volume of a focal zone 17 of the first and second focused acoustic energies, e.g., so that the entire sample is located within the focal zone. However, in other embodiments, the sample may be flowed through a treatment zone of the vessel, e.g., the vessel 4 may have an inlet 41 and an outlet 42 and the liquid sample may flow through the vessel 4 from the inlet 41 to the outlet 42 as shown in FIG. 2. Thus, the sample may have a larger volume, e.g., 1 liter or more, while only a relatively small volume of sample (such as 100 milliliters or less) is subjected to acoustic treatment at any given time. In some cases, the liquid sample may flow through the vessel 4 at a rate of 12 milliliters per minute or less.

Regarding purposes to which aspects of the disclosure may be employed, many binding reactions can be enhanced with acoustic treatments in accordance with aspects of the present disclosure. For example, binding reactions involve binding together two or more molecules, two nucleic acid molecules, by hybridization and/or by other non-covalent binding. Binding reactions are employed, for example, in an assay to detect binding, such as a specific staining reaction, where one nucleotide molecule is a primer and the other is a substrate molecule to be replicated, or in a binding interaction involving an antibody and the molecule it binds, such as an immunoassay. Reactions also can involve binding of a substrate and a ligand. For example, a substrate such as an antibody or receptor can be immobilized on a support surface, for use in purification or separation techniques of epitopes, ligands, and other molecules.

In certain embodiments, temperature, mixing, or both can be controlled with ultrasonic energy to enhance a chemical reaction. For example, the association rate between a ligand present in a sample to be treated and a binding partner on a bead or other support in the sample can be accelerated. In another example, an assay may be performed where temperature is increased or maintained and mixing is increased to improve association of two or more molecules compared to ambient conditions. It is possible to combine the various aspects of the embodiments described herein by first subjecting a mixture to heat and mixing in order to separate a ligand or analyte in the mixture from endogenous binding partners in the mixture. The temperature, mixing, or both, may be changed from the initial condition to enhance ligand complex formation with a binding partner relative to ligand/endogenous binding partner complex formation. Where temperature is increased to enhance some reactions, the sample temperature may be later reduced, e.g., to slow or stop the reaction and/or enhance stability of the resulting compounds.

Focused acoustic energy can be used to enhance separations. As noted elsewhere, sonic foci can be used to affect fluid flow, which is an important element of many separation processes, such as chromatography including gas chromatography, size exclusion chromatography, ion exchange chromatography, and other known forms, including filed-flow fractionation. The ability to remotely modulate and/or reduce or eliminate velocity and concentration gradients of a flowing stream may be applicable in a wide variety of situations.

Acoustic treatment can be used to enhance reaction rates in a viscous medium, by providing remote stirring on a micro scale with minimal heating and/or sample damage. Flow at the walls of a vessel may be useful in promoting micro and larger scale stirring whether with or without significant heat transfer. Likewise, any bimolecular (second-order) reaction where the reactants are not mixed at a molecular scale, each homogenously dissolved in the same phase, potentially can be accelerated by sonic stirring. At scales larger than a few nanometers, convection or stirring can potentially minimize local concentration gradients and thereby increase the rate of reaction. This effect can be important when both reactants are macromolecules, such as an antibody and a large target for the antibody, such as a cell, since their diffusion rates are relatively slow and desorption rates may not be significant.

These advantages may be realized inexpensively on multiple samples in an array, such as a microtiter plate. The use of remote sonic mixing provides a substantially instantaneous start time to a reaction when the sample and analytical reagents are of different densities, because in small vessels, such as the wells of a 96 or 384 well plate, little mixing will occur when a normal-density sample (about 1 g/cc) is layered over a higher-density reagent mixture. Remote sonic mixing can start the reaction at a defined time and control its rate, when required. Stepping and dithering functions may allow multiple readings of the progress of the reaction to be made. The mode of detecting reaction conditions can be varied between samples if necessary. In fact, observations by multiple monitoring techniques, such as the use of differing optical techniques, can be used on the same sample at each pass through one or more detection regions.

Focused acoustic treatment in accordance with aspects of the present disclosure may be useful for preparing formulations having a narrow particle size distribution. Such formulations may include suspensions and/or emulsions having particles that are submicron in size and may have applications for therapeutic use, such as delivery systems for bioactive agents (e.g., liposomes, micelles, etc.). Controlling heat transfer in a focused acoustic processing system using the methods described herein may enhance the ability to suitably prepare formulations in an advantageous manner (e.g., repeatable, short processing times, high yield, etc.).

In some embodiments, enhancing heat transfer between the wall of a processing vessel and a fluid upon focused acoustic treatment may also be useful for initiating (e.g., forming nucleation sites) and augmenting (nano)crystalline growth. For example, crystalline particles may be formed as a suspension of particles (e.g., submicron in size) in a liquid solution. In some cases, though not required, (nano)crystalline particles prepared in accordance with aspects described herein may be useful for therapeutic delivery of bioactive agents.

Example 1

In one example, a sample was flowed through a treatment vessel arranged like that in FIG. 2 (except that cooling liquid was not circulated, and instead the vessel was immersed in a liquid coupling medium as in FIG. 1) and was treated by acoustic energy having three different PIP and DC settings, i.e., (1) a PIP of 35 and DC of 50; (2) a PIP of 175 and DC of 10; and (3) a PIP of 350 and DC of 5. In all cases, the sample was plain water, and was flowed through the treatment vessel at a rate of about 11.5 milliliters per minute. The acoustic energy had a CPB of 1000, and the liquid coupling medium had a constant temperature of about 3.4 degrees C. for all three treatment periods. The temperature of sample flowing into the treatment vessel was about 9.5 degrees C. for all treatment periods.

The temperature of the sample as the sample was flowing out of the treatment vessel was detected and it was found that the output temperature for treatment period (1) was about 8.6 degrees C. at steady state, for treatment period (2) was about 7.6 degrees C. at steady state, and for treatment period (3) was about 7.45 degrees C. at steady state. In all cases, the average incident power applied to the sample was the same, i.e., 17.5 Watts, but increased cooling rates were exhibited for increased PIP settings.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

The use of "including," "comprising," "having," "containing," "involving," and/or variations thereof herein, is meant to encompass the items listed thereafter and equivalents thereof as well as additional items.

It should also be understood that, unless clearly indicated to the contrary, in any methods claimed herein that include more than one step or act, the order of the steps or acts of the method is not necessarily limited to the order in which the steps or acts of the method are recited.

While aspects of the present disclosure have been described with reference to various illustrative embodiments, such aspects are not limited to the embodiments described. Thus, it is evident that many alternatives, modifications, and variations of the embodiments described will be apparent to those skilled in the art. Accordingly, embodiments as set forth herein are intended to be illustrative, not limiting. Various changes may be made without departing from the spirit of aspects of the present disclosure.

What is claimed is:

1. A method for acoustic treatment of a sample contained in a vessel, comprising:
   providing a vessel containing a liquid sample at a holder of an acoustic treatment apparatus, the vessel having a wall in contact with a thermal transfer medium of the acoustic treatment apparatus, the thermal transfer medium having a thermal transfer medium temperature;
   exposing the liquid sample to a first focused acoustic energy for a first period of time, the first focused acoustic energy being transmitted through the vessel to the liquid sample, the first focused acoustic energy having a first peak incident power (PIP) and a first duty cycle, and the liquid sample having a first temperature at an end of the first period of time, the first temperature being greater than the thermal transfer medium temperature, exposing the liquid sample to the first focused acoustic energy including transferring heat from the liquid sample to the thermal transfer medium during the first period of time at a first rate; and
   exposing the liquid sample to a second focused acoustic energy for a second period of time, the second focused acoustic energy being transmitted through the vessel to the liquid sample, the second focused acoustic energy having a second peak incident power (PIP) and a second duty cycle, the second PIP being larger than the first PIP, and the liquid sample having a second temperature at an end of the second period of time that is lower than the first temperature, exposing the liquid sample to the second focused acoustic energy including transferring heat from the liquid sample to the thermal transfer medium during the second period of time at a second rate that is faster than the first rate,
   wherein the thermal transfer medium temperature is the same for the first and second periods of time, and
   wherein a first average incident power for the first focused acoustic energy during the first period of time is equal to or less than a second average incident power for the second focused acoustic energy during the second period of time.

2. The method of claim 1, wherein the first duty cycle is greater than the second duty cycle.

3. The method of claim 1, wherein a first total energy delivered to the liquid sample during the first period of time is equal to or less than a second total energy delivered to the liquid sample during the second period of time.

4. The method of claim 1, wherein a first average incident power for the first focused acoustic energy during the first period of time and a second average incident power for the second focused acoustic energy during the second period of time are both less than 20 Watts.

5. The method of claim 1, wherein the thermal transfer medium temperature is less than the second temperature.

6. The method of claim 1, wherein the thermal transfer medium temperature is 4 degrees C. or less.

7. The method of claim 1, wherein a volume of the liquid sample is 10 milliliters or less.

8. The method of claim 1, wherein a volume of the liquid sample is less than a volume of a focal zone of the first and second focused acoustic energies.

9. The method of claim 1, wherein the first and second focused acoustic energies have a same cycles per burst.

10. The method of claim 1, wherein the vessel has an inlet and an outlet and the liquid sample flows through the vessel from the inlet to the outlet.

11. The method of claim 10, wherein the liquid sample flows through the vessel at a rate of 12 milliliters per minute or less.

12. The method of claim 1, wherein the thermal transfer medium is a coupling medium and the acoustic energy is transmitted through the coupling medium to the vessel.

13. The method of claim 12, wherein the coupling medium receives heat from the liquid sample.

14. The method of claim 1, wherein the thermal transfer medium is circulated relative to the vessel.

15. The method of claim 1, wherein the vessel is a closed tube that contains the liquid sample.

16. A method for acoustic treatment of a sample contained in a vessel, comprising:

providing a vessel containing a liquid sample at a holder of an acoustic treatment apparatus, the vessel having a wall in contact with a thermal transfer medium of the acoustic treatment apparatus, the thermal transfer medium having a thermal transfer medium temperature;

exposing the liquid sample to a focused acoustic energy for a first period of time, the focused acoustic energy being transmitted through the wall of the vessel to the liquid sample, the focused acoustic energy having a peak incident power (PIP) and a duty cycle, exposing the liquid sample to the focused acoustic energy including transferring heat from the liquid sample to the thermal transfer medium during the first period of time to cool the liquid sample at a first rate; and increasing the PIP of the focused acoustic energy during a second period of time to transfer heat from the liquid sample to the thermal transfer medium to cool the liquid sample at a second rate that is faster than the first rate, wherein the thermal transfer medium temperature is the same for the first and second periods of time.

* * * * *